US012592382B2

(12) United States Patent
Scott et al.

(10) Patent No.: US 12,592,382 B2
(45) Date of Patent: Mar. 31, 2026

(54) ELECTROCHEMICAL CELLS WITH LITHIUM ALLOY ANODES

(71) Applicant: Medtronic, Inc., Minneapolis, MN (US)

(72) Inventors: Erik R. Scott, Maple Grove, MN (US); Prabhakar A. Tamirisa, Brooklyn Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 725 days.

(21) Appl. No.: 17/963,907

(22) Filed: Oct. 11, 2022

(65) Prior Publication Data

US 2024/0120473 A1 Apr. 11, 2024

(51) Int. Cl.
*H01M 4/40* (2006.01)
*A61N 1/05* (2006.01)
*H01M 10/0525* (2010.01)
*H01M 10/42* (2006.01)
*H01M 50/46* (2021.01)
*H01M 4/02* (2006.01)

(52) U.S. Cl.
CPC .......... *H01M 4/405* (2013.01); *A61N 1/0563* (2013.01); *H01M 10/0525* (2013.01); *H01M 10/4235* (2013.01); *H01M 50/46* (2021.01); *H01M 2004/027* (2013.01)

(58) Field of Classification Search
CPC .. H01M 4/405; H01M 50/46; H01M 10/0525; H01M 10/4235; H01M 2004/027; A61N 1/0563

USPC ...................................................... 429/231.95
See application file for complete search history.

(56) References Cited

U.S. PATENT DOCUMENTS

| | | | |
|---|---|---|---|
| 4,259,420 A | 3/1981 | Feiman | |
| 5,350,647 A | 9/1994 | Hope | |
| 5,858,573 A | 1/1999 | Abraham et al. | |
| 6,322,744 B1 | 11/2001 | Kelley et al. | |
| 9,341,678 B2 * | 5/2016 | Kim ...................... | G01R 31/382 |
| 2016/0285128 A1 * | 9/2016 | Matsui ................... | H01M 4/405 |
| 2018/0196421 A1 * | 7/2018 | Carlhoff ................ | B60W 30/00 |
| 2018/0358620 A1 | 12/2018 | O'Neil et al. | |
| 2020/0127324 A1 * | 4/2020 | Ryu ................... | H01M 10/0525 |
| 2020/0343583 A1 * | 10/2020 | Li ...................... | H01M 10/0562 |
| 2020/0365887 A1 | 11/2020 | Zaghib | |
| 2022/0190314 A1 * | 6/2022 | Uchiyama ......... | H01M 10/0567 |

OTHER PUBLICATIONS

Gu et al., "Li-containing alloys beneficial for stabilizing lithium anode: A review" Engineering Reports, 2021; 3:e12339. 24 pages.

(Continued)

*Primary Examiner* — James M Erwin

(74) *Attorney, Agent, or Firm* — Mueting Raasch Group

(57) ABSTRACT

Electrochemical cells and methods of preventing overheating of the same are disclosed. An electrochemical cell may include a cathode and an anode. The anode may include a lithium alloy. The anode may be configured to reduce a maximum rate of ion transfer between the anode and the cathode in response to an occurrence of a fault condition. The lithium alloy may comprise at least 70 weight percent lithium to 99 weight percent lithium.

18 Claims, 6 Drawing Sheets

(56)          References Cited

OTHER PUBLICATIONS

Shi et al., "Electrochemical properties of Li—Mg alloy electrodes for lithium batteries" J Power Sources, 2001; 92:70-80.
Choi et al., "Marginal Magnesium Doping for High-Performance Lithium Metal Batteries" Adv. Energy Mater., 2019; 9:1902278. 10 pages.
Obrovac et al., "Alloy Negative Electrodes for Li-Ion Batteries" Chem. Rev., 2014; 114:11444-11502.
International Search Report and Written Opinion for PCT/US2023/034787 dated Mar. 18, 2024 (13 pages).

* cited by examiner

ELECTROCHEMICAL CELLS WITH LITHIUM ALLOY ANODES

FIELD

The present disclosure relates to, among other things, batteries or electrochemical cells.

TECHNICAL BACKGROUND

Batteries or electrochemical cells are generally used to provide power to devices when wired connections to external power sources may be undesirable or inconvenient. For example, batteries may be used in portable devices such as laptops and mobile phones or in implantable medical devices where constant connection to external power sources may be cumbersome or excessively restrictive. Some devices that utilize batteries or electrochemical cells as a power source may require relatively small batteries or cells to provide relatively large amounts of power. In general, high-power batteries generally include electrodes with large surface areas relative to their size. However, the ability to supply large amounts of power generally coincides with the ability to generate large amounts of heat that may be undesirable in many applications. Accordingly, high-power batteries or cells may be subject to design constraints such as limits to electrode surface areas to limit the amount of heat that can be generated by such high-power batteries or cells. Limits on electrode surface areas may result in limits on the power output of such batteries or cells.

BRIEF SUMMARY

The present disclosure describes, among other things, batteries or electrochemical cells with a relatively high-power output capability and a built-in fault condition response using anodes that include a lithium alloy. The use of some lithium alloys as anodes in batteries or electrochemical cells has surprising effects. For example, such lithium alloy anodes may allow batteries or cells to provide power in amounts required by various devices under typical operating conditions while restricting the amount of power supplied during a fault condition. Accordingly, the batteries and electrochemical cells described herein can supply enough power to devices when operated within the typical or expected power ranges of such devices, even when such power ranges are relatively high, and also limit the amount of power supplied by the batteries or cells when devices attempt to draw power in excess of the expected ranges, or the battery experiences a fault condition such as a short. Thus, the batteries and electrochemical cells described herein include a built-in overheat protection without the need to limit electrode surface areas. Furthermore, power output of batteries and electrochemical cells can be tuned or increased to accommodate the needs of devices with high-power requirements while and tuned to limit power output in the event of a failure condition to prevent excessive heat generation. Additionally, the batteries and electrochemical cells described herein may reverse the power output limitations if the failure condition ends or is otherwise corrected.

Described herein, among other things, is an electrochemical cell comprising a cathode and an anode. The anode may include a lithium alloy. The anode may be configured to reduce a maximum rate of ion transfer between the anode and the cathode in response to an occurrence of a fault condition. The lithium alloy may comprise at least 70 weight percent lithium to 99 weight percent lithium.

In general, in one aspect, the present disclosure describes an implantable medical device comprising a housing, one or more electrical components disposed in the housing, and one or more electrochemical cells electrically coupled to at least one electrical component of the one or more electrical components. Each of the one or more electrochemical cells may comprise a cathode, an anode, a separator, and an electrolyte. The anode may comprise a lithium alloy. Additionally, the anode may be configured to reduce a maximum rate of ion transfer between the anode and the cathode in response to an occurrence of a fault condition. The lithium alloy may comprise at least 70 weight percent lithium to 99 weight percent lithium. The separator may be arranged between the anode and the cathode to prevent direct contact between the anode and the cathode. The electrolyte may facilitate transport of charged ions between the anode and the cathode.

In general, in one aspect, the present disclosure describes a method to prevent overheating of an electrochemical cell. The electrochemical cell may comprise a cathode, an anode, a separator, and an electrolyte. The anode may comprise a lithium alloy. The lithium alloy may comprise at least 70 weight percent lithium to 99 weight percent lithium. Additionally, the lithium alloy may be configured to reduce a maximum rate of ion transfer between the anode and the cathode in response to an occurrence of a fault condition. The separator may be arranged between the anode and the cathode to prevent direct contact between the anode and the cathode. The electrolyte may facilitate transport of charged ions between the anode and the cathode. The method may comprise providing power using the electrochemical cell and adjusting, using the anode, a maximum rate of ion transfer between the cathode and the anode from a standard maximum rate to a reduced maximum rate response to an occurrence of a fault condition of the electrochemical cell.

Advantages and additional features of the subject matter of the present disclosure will be set forth in the detailed description which follows, and in part will be readily apparent to those skilled in the art from that description or recognized by practicing the subject matter of the present disclosure as described herein, including the detailed description which follows, the claims, as well as the appended drawings.

It is to be understood that both the foregoing general description and the following detailed description present embodiments of the subject matter of the present disclosure, and are intended to provide an overview or framework for understanding the nature and character of the subject matter of the present disclosure as it is claimed. The accompanying drawings are included to provide a further understanding of the subject matter of the present disclosure and are incorporated into and constitute a part of this specification. The drawings illustrate various embodiments of the subject matter of the present disclosure and together with the description serve to explain the principles and operations of the subject matter of the present disclosure. Additionally, the drawings and descriptions are meant to be merely illustrative and are not intended to limit the scope of the claims in any manner.

BRIEF DESCRIPTION OF THE DRAWINGS

The following detailed description of specific embodiments of the present disclosure can be best understood when read in conjunction with the following drawings, in which.

Figure 1:
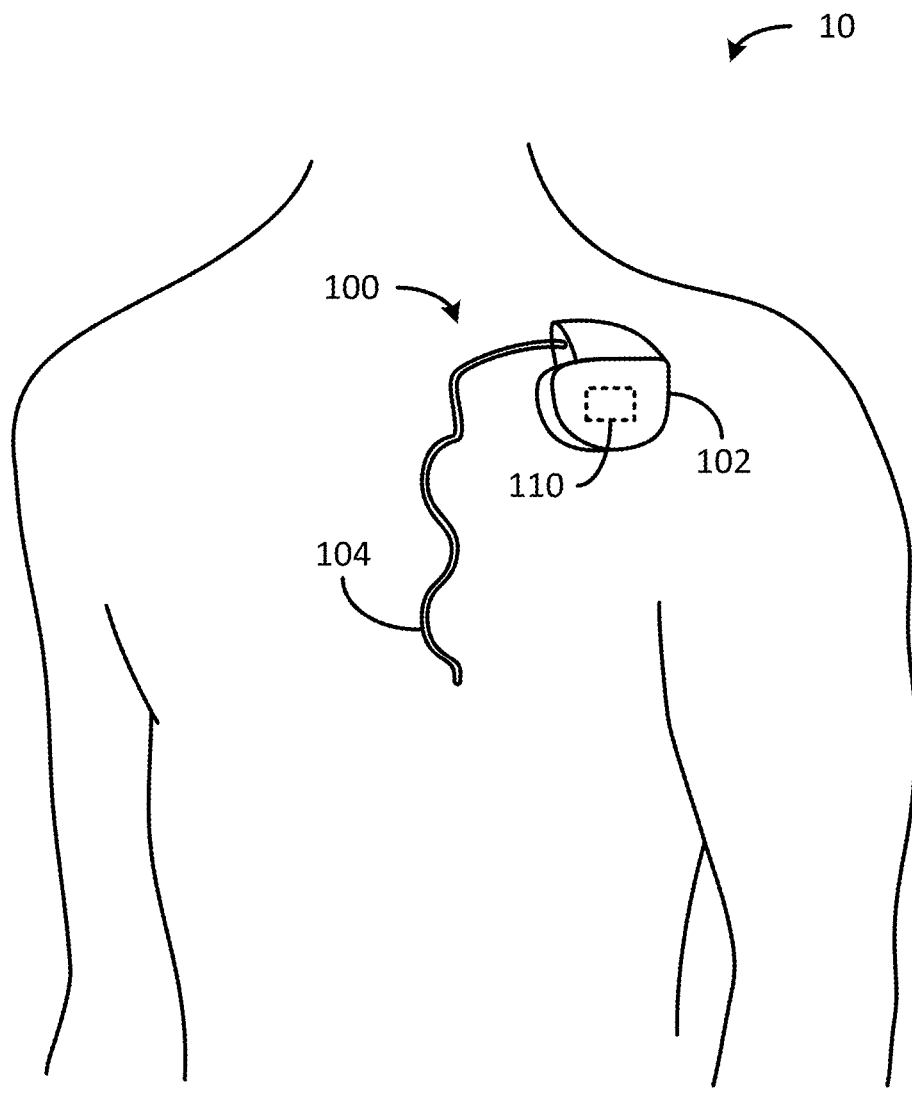
FIG. 1 is a conceptual drawing illustrating an embodiment of a battery used in an implantable medical device.

The schematic drawing is not necessarily to scale.

DETAILED DESCRIPTION

Reference will now be made in greater detail to various embodiments of the subject matter of the present disclosure, one or more embodiments of which are illustrated in the accompanying drawings. Like numbers used in the figures refer to like components and steps. However, it will be understood that the use of a number to refer to a component in a given figure is not intended to limit the component in another figure labeled with the same number. In addition, the use of different numbers to refer to components in different figures is not intended to indicate that the different numbered components cannot be the same or similar to other numbered components.

Batteries or electrochemical cells for use in devices or applications that require relatively large amounts of energy in a short period of time may be referred to as high-power batteries or high-power electrochemical cells. High-power batteries or cells may include electrodes with relatively large surface areas that allow larger amounts of power to be provided for high-power applications when compared to batteries and cells with electrodes that have larger thicknesses and smaller surface areas within the same volume. High-power applications may include therapeutic pulse delivery, electric motors capable of rapid acceleration, etc. In general, high-power batteries or cells are also capable of generating relatively large amounts of heat that may be undesirable, particularly in a fault condition. For example, in a shorted condition, high-power batteries or cells that lack robust overheat protections can generate enough heat to damage the devices they power and provide unwanted heat to a surrounding environment.

One way to prevent overheating of high-power batteries and cells is to restrict or limit the surface area of the electrodes of such batteries or cells to a surface area smaller than what the batteries or cells can accommodate. However, such surface area restrictions may also limit the amount of power that can be supplied by the high-power batteries or cells. Accordingly, some devices may be limited by the amount of power that a battery or cell with limited electrode surface area can provide to avoid generation of unwanted heat in a failure condition. However, batteries or electro-chemical cells that include a lithium alloy as described herein can prevent overheating while allowing the electrodes of such electrochemical cells to have as much surface area as physically possible. Accordingly, such batteries or cells that include anodes with a lithium alloy as described herein may provide more power than batteries or cells with limited electrode surface areas in the same form factor without sacrificing overheat protections.

Batteries or electrochemical cells as described herein may include anodes have a lithium alloy. In contrast, design considerations for typical lithium batteries generally attempt to achieve anodes of pure lithium to boost efficiency. However, as will be demonstrated herein, the present inventors have surprisingly found that the use of some lithium alloys as anodes of batteries or electrochemical cells allows the batteries or cells to perform similarly to cells that have substantially pure lithium anodes during normal operating conditions but reduce the rate of ion transfer when high levels of power are drawn or provided for longer than normal conditions would require.

Without wishing to be bound by theory, it has been found that some lithium alloy anodes (used interchangeably herein with anodes that include a lithium alloy) behave similar to substantially pure lithium anodes but as high levels of power draw are maintained, a maximum rate of ion transfer between the anode and the cathode may become limited. In other words, lithium alloy anodes as described herein may reduce the maximum rate of ion transfer between the anode and the cathode from a standard rate to a reduced rate in response to a fault condition. By limiting the rate of ion transfer, a measured internal resistance of such batteries or cells may increase while the provided power, current, and heat decrease. Furthermore, when the fault condition is corrected, the maximum rate of ion transfer may return to the standard rate from the reduced rate.

Additionally, anodes that include a lithium alloy may also reduce the occurrence of conductive bridges formed by thermal gradients in electrochemical cells. Thermal gradients in lithium electrochemical cells can lead to re-arrangement of lithium and lithium plating within a cell due to the formation of a local thermogalvanic cell. Such lithium plating can create conductive bridges that may lead to shorts within lithium electrochemical cells. A conventional method in lithium battery designs to avoid such lithium plating is to create a tortuous path between cathode and anode plates. The addition of an alloying element to lithium may change the fundamental dissolution and deposition kinetics of lithium. For example, use of lithium alloy in anodes may improve cycle life of lithium metal rechargeable batteries by suppressing dendritic growth of lithium. Accordingly, the anodes that include lithium alloys as described herein may reduce the occurrence of conductive bridges and, therefore, internal electrical shorts when thermal gradients are present. As such, the design burden of creating a tortuous path may be reduced, allowing more design freedom that may lead to more efficient designs and ease of assembly.

An embodiment of a device or system that includes a battery with a lithium alloy anode as described herein, is depicted in FIG. 1. FIG. 1 shows a conceptual drawing illustrating a device or system 100 in conjunction with a patient 10. As depicted in FIG. 1, the device 100 includes a housing 102 that defines the exterior of an implantable medical device. The device 100 may be or may be included in, any suitable implantable medical device such as, for example, implantable pulse generators, implantable cardio-verter defibrillators, implantable cardiac contractility modu-lators, implantable neurostimulators, implantable mechani-cal assist devices, etc.

The device 100 may also include one or more leads 104 to deliver therapeutic electrical pulses to desired treatment areas of the patient 10. The leads 104 may include one or more electrodes (not shown) to facilitate delivery of the therapeutic electrical pulses to the desired treatment areas. In one or more embodiments, the device 100 may include one or more electrodes without any leads. For example, when the device 100 can be implanted at the desired treatment area, leads may not be needed to deliver the therapeutic electrical pulses.

The device 100 may include one or more electrical components disposed in the housing 102. The one or more electrical components may include one or more pulse generators, switches, passive electrical components (e.g., capacitors, inductors, or resistors), digital logic circuits, controllers, processors, or other components to facilitate operation of the device 100. Additionally, the device 100 may include one or more electrochemical cells 110 electrically coupled to at least one electrical component of the one or more electrical components. In other words, the one or more electrochemical cells may be configured to provide power to the at least one electrical component.

Figure 2:
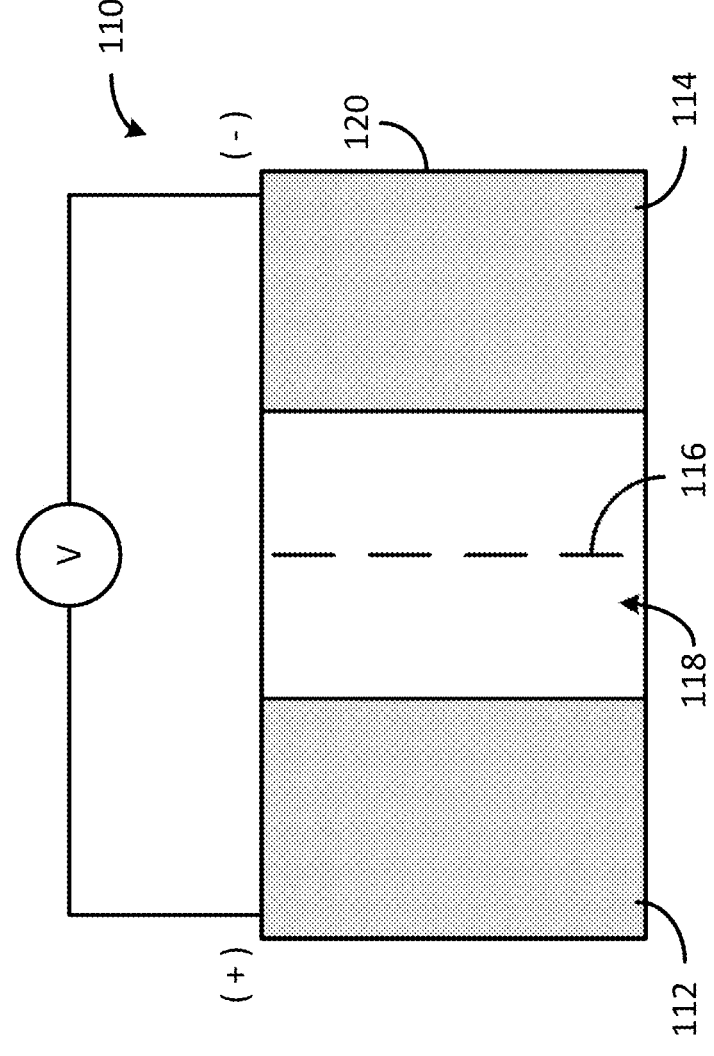
FIG. 2 is a schematic diagram of an embodiment of an electrochemical cell.

A schematic representation of an embodiment of an electrochemical cell 110 is depicted in FIG. 2. The electrochemical cell 110 may be, or may form a single cell of, a lithium battery. The electrochemical cell 110 may be any suitable rechargeable lithium electrochemical cell. For example, the electrochemical cell 110 may be a lithium-ion electrochemical cell, a lithium metal electrochemical cell, a lithium polymer electrochemical cell, or other lithium electrochemical cell. Accordingly, the batteries described herein may be, for example, lithium-ion batteries, a lithium metal batteries, a lithium polymer batteries, or other lithium batteries. Additionally, the electrochemical cell 110 may be a primary cell (e.g., non-rechargeable) or a secondary cell (e.g., rechargeable).

The electrochemical cell 110 may include a cathode 112, an anode 114, a separator 116, and an electrolyte 118. The electrochemical cell 110 may also include a cell housing 120 that defines the exterior of the electrochemical cell 110. In other words, each of the cathode 112, the anode 114, the separator 116, and the electrolyte 118 may be disposed in the cell housing 120. The cathode 112 and the anode 114 may be provided as relatively flat or planar plates, wrapped or wound in a spiral or other configuration (e.g., an oval configuration), or as a folded configuration. The separator 116 (e.g., a polymeric microporous separator) may be arranged between the anode 114 and the cathode 112 to prevent direct contact between the anode 114 and the cathode 112.

The cathode 112 may include any one or more materials such as, for example, silver vanadium oxide ($Ag_2V_4O_{11}$), carbon monofluoride (CFx), thionyl chloride ($SOCl_2$) manganese dioxide ($MnO_2$), silver vanadium oxyfluoride ($Ag_2V_2O_6F_2$), lithium-metal oxides (e.g., LiCoO2, LiMn2O4, Li(NixMnyCoz)O2, etc.), other vanadium oxides, olivines (e.g., LiFePO4), sulfides, etc. The particular materials used or included in the cathode 112 may depend on whether the electrochemical cell 110 is a primary or a secondary cell. For instance, as part of a primary cell, the cathode 112 may include, for example, silver vanadium oxide ($Ag_2V_4O_{11}$), carbon monofluoride (CFx), thionyl chloride ($SOCl_2$) manganese dioxide ($MnO_2$), silver vanadium oxyfluoride ($Ag_2V_2O_6F_2$), or other metal oxides or halides. As part of a secondary cell, the cathode 112 may include, for example, lithium-metal oxides (e.g., LiCoO2, LiMn2O4, Li(NixMnyCoz)O2, etc.), vanadium oxides, olivines (e.g., LiFePO4), sulfides, etc. In one or more embodiments, the cathode 112 may include a mixture of cathode materials, such as a mixture comprising CFx with either $Ag_2V_4O_{11}$ or $MnO_2$.

The anode 114 may include a lithium alloy. The anode 114 may be substantially free of any materials or impurities in addition to the lithium alloy. The lithium alloy may include at least 70 weight percent lithium and no greater than 99.9 weight percent lithium or any suitable range therebetween. The lithium alloy of the anode 114 may include at least 70 weight percent lithium, at least 75 weight percent lithium, at least 80 weight percent lithium, at least 85 weight percent lithium, at least 90 weight percent lithium, or at least 95 weight percent lithium. The lithium alloy of the anode 114 may include no greater than 99.9 weight percent lithium, no greater than 99 weight percent lithium, no greater than 95 weight percent lithium, no greater than 90 weight percent lithium, no greater than 85 weight percent lithium, no greater than 80 weight percent lithium, or no greater than 75 weight percent lithium. In one or more embodiments, the lithium alloy of the anode 114 may include at least 70 weight percent lithium and no greater than 99 weight percent lithium. In one or more embodiments, the lithium alloy of the anode 114 may include at least 85 weight percent lithium and no greater than 95 weight percent lithium. In one or more embodiments, the lithium alloy of the anode 114 may include at least 88 weight percent lithium and no greater than 92 weight percent lithium.

The lithium alloy of the anode 114 may also include one or more of magnesium, silver, zinc, aluminum, tin, silicon, or other elements that are soluble in lithium at a level of at least 1 weight percent. In one or more embodiments, the lithium alloy of the anode may be a binary alloy. In other words, the lithium alloy of the anode 114, may include lithium and one other element while being substantially free of any other materials or impurities. The one other element of the binary lithium alloy may include one of, for example, magnesium, silver, aluminum, tin, or silicon. The binary lithium alloy may include at least 0.01 weight percent of the other element and no greater than 30 weight percent of the other element or any suitable weight percent therebetween of the other element. The binary lithium alloy may include at least 0.01 weight percent of the other element, at least 1 weight percent of the other element, at least 5 weight percent of the other element, at least 10 weight percent of the other element, at least 15 weight percent of the other element, at least 20 weight percent of the other element, or at least 25 weight percent of the other element. The binary lithium alloy may include no greater than 30 weight percent of the other element, no greater than 25 weight percent of the other element, no greater than 20 weight percent of the other element, no greater than 15 weight percent of the other element, no greater than 10 weight percent of the other element, or no greater than 5 weight percent of the other element. In one or more embodiments, the binary lithium alloy of the anode 114 may include at least 1 weight percent of the other element and no greater than 30 weight percent of the other element. In one or more embodiments, the lithium alloy of the anode 114 may include at least 5 weight percent of the other element and no greater than 15 weight percent of the other element. In one or more embodiments, the lithium alloy of the anode 114 may include at least 8 weight percent of the other element and no greater than 12 weight percent of the other element.

In one or more embodiments, the lithium alloy of the anode 114 may include at least 0.01 weight percent of magnesium and no greater than 30 weight percent of magnesium or any suitable weight percent therebetween of magnesium. The lithium alloy may include at least 0.01 weight percent of magnesium, at least 1 weight percent of magnesium, at least 5 weight percent of magnesium, at least 10 weight percent of magnesium, at least 15 weight percent of magnesium, at least 20 weight percent of magnesium, or at least 25 weight percent of magnesium. The lithium alloy may include no greater than 30 weight percent of magnesium, no greater than 25 weight percent of magnesium, no greater than 20 weight percent of magnesium, no greater than 15 weight percent of magnesium, no greater than 10 weight percent of magnesium, or no greater than 5 weight percent of magnesium. In one or more embodiments, the lithium alloy of the anode 114 may include at least 1 weight percent of magnesium and no greater than 30 weight percent of magnesium. In one or more embodiments, the lithium alloy of the anode 114 may include at least 5 weight percent of magnesium and no greater than 15 weight percent of magnesium. In one or more embodiments, the lithium alloy of the anode 114 may include at least 8 weight percent of magnesium and no greater than 12 weight percent of magnesium.

In one or more embodiments, the lithium alloy of the anode 114 may include two or more elements in addition to lithium. In other words, the lithium alloy may include lithium and additional elements. The additional elements may include two or more of, for example, magnesium, silver, zinc, aluminum, tin, and silicon. The lithium alloy may include at least 0.01 weight percent of the additional elements, at least 1 weight percent of the additional elements, at least 5 weight percent of the additional elements, at least 10 weight percent of the additional elements, at least 15 weight percent of the additional elements, at least 20 weight percent of the additional elements, or at least 25 weight percent of the additional elements. The lithium alloy may include no greater than 30 weight percent of the additional elements, no greater than 25 weight percent of the additional elements, no greater than 20 weight percent of the additional elements, no greater than 15 weight percent of the additional elements, no greater than 10 weight percent of the additional elements, or no greater than 5 weight percent of the additional elements. In one or more embodiments, the lithium alloy of the anode 114 may include at least 1 weight percent of the additional elements and no greater than 30 weight percent of the additional elements. In one or more embodiments, the lithium alloy of the anode 114 may include at least 5 weight percent of the additional elements and no greater than 15 weight percent of the additional elements. In one or more embodiments, the lithium alloy of the anode 114 may include at least 8 weight percent of the additional elements and no greater than 12 weight percent of the additional elements.

In one or more embodiments, the anode 114 may include material or structure in addition to the lithium alloy. Such additional material or structure may be referred to as an anode core. Regardless of any additional material or structure, the anode 114 may include no less than 70 weight percent lithium and no greater than 99 weight percent lithium. The anode core may include substantially pure lithium. The lithium alloy may define an outer surface layer of the anode 114. In other words, the lithium alloy may define a layer that partially cover or completely surround the anode core. In one or more embodiments, the lithium alloy completely surrounds the anode core. An alloy gradient may be formed or defined between the lithium alloy and the anode core. The alloy gradient may be formed during a manufacturing process of the anode 114. Additionally, the alloy gradient may be formed over time as the electrochemical cell 110 is charged or discharged. The alloy gradient may be a blending of the materials of the lithium alloy and the anode core at or near an interface between the lithium alloy and the anode core. In other words, materials of the lithium alloy may at least partially diffuse into the anode core.

During charging and discharging of the electrochemical cell 110, lithium ions may move between the cathode 112 and the anode 114. Such movement of lithium ions between the cathode 112 and the anode 114 may be referred to as ion transfer. For example, when the electrochemical cell 110 is discharged, lithium ions flow from the anode 114 to the cathode 112. In contrast, when the electrochemical cell 110 is charged, lithium ions flow from the cathode 112 to the anode 114. While the separator 116 may prevent direct contact between the cathode 112 and the anode 114, the separator may permit the flow of ions between the anode 114 and the cathode 112. Furthermore, the electrolyte 118 may facilitate transport of ions between the anode 114 and the cathode 112.

The electrolyte 118 may be disposed in the cell housing 120. The electrolyte 118 may generally fill at least a portion of any space inside the cell housing 120 that is not filled by the other components (e.g., the cathode 112, the anode 114, the separator 116, insulators, conductors, etc.) of the electrochemical cell 110. The electrolyte 118 may have an electrical potential. When the cathode 112 and the anode 114 are electrically isolated from the cell housing 120, the cell housing 120 may float at the electrical potential of the electrolyte. The electrolyte 118 may be one or more of, for example, a liquid, a gel, a paste, etc. The material composition of the electrolyte may depend on a cell type of the electrochemical cell 110. The electrolyte 118 may include, for example, lithium salt, sulfuric acid, fluorinated sulfone, or other suitable electrolyte.

While the electrolyte 118 may facilitate or otherwise provide a medium for ion transfer between the cathode 112 and the anode 114, the composition of the anode 114 may influence a maximum rate of ion transfer between the cathode 112 and the anode 114. In general, the more lithium available on surfaces of the anode 114 for ion transfer the greater the maximum rate of ion transfer between the cathode 112 and the anode 114. Accordingly, anodes with greater surface area may have a higher maximum rate of ion transfer than anodes with smaller surface areas. Additionally, a higher maximum rate of ion transfer may allow for a higher maximum power output than electrochemical cells with lower maximum rates of ion transfer. While the surface area of anodes is generally static in electrochemical cells (e.g., electrochemical cell 110), the lithium available for ion transfer on surfaces of the anode 114 may be dynamic allowing the maximum rate of ion transfer between the anode 114 and the cathode 112 to be adjusted while in use.

The anode 114 may be configured to reduce a maximum rate of ion transfer between the anode 114 and the cathode 112 from a standard rate to a reduced rate in response to an occurrence of a fault condition. Reduction of the maximum rate of ion transfer may limit amount of power that can be supplied by the electrochemical cell and, consequently, the amount of heat produced by the electrochemical cell 110. The standard rate may be a rate of ion transfer that corresponds to the highest rate of ion transfer and power output of the electrochemical cell 110 facilitated by the size of the surface area of the anode 114. The reduced rate may be rate of ion transfer that limits power output of the electrochemical cell 110 to an amount that will prevent overheating of the electrochemical cell 110 even if such limited power output is maintained for extended periods of time. In other words, a maximum power output of the electrochemical cell 110 may be limited by the reduced rate of ion transfer such that maximum power output does not heat the electrochemical cell 110 faster than such heat can be dissipated from the electrochemical cell 110.

The fault condition may include any condition that causes the electrochemical cell 110 to provide power in excess of what is expected under typical device or system operation (e.g., device 100 of FIG. 1). The fault condition may include an electrical short in the electrochemical cell 110 or electronic components or devices to which electrochemical cell 110 provides power. The fault condition may also include any condition that causes the electrochemical cell 110 to provide power above a threshold amount for a predetermined period of time. Such conditions may include programming errors in an electrically coupled device or system (e.g., device 100 of FIG. 1), mechanical failures of the electrically coupled device or system, unexpected parameter settings of the electrically coupled device or system, mechanical failures of the electrochemical cell 110, etc. The threshold amount of power may be based on an amount of power that is capable of heating the electrochemical cell 110 faster than heat can dissipate from the electrochemical cell 110.

The anode 114 may also be configured to reverse the reduction of the maximum rate of ion transfer in response to a correction of the fault condition. In other words, the anode 114 may be configured to increase the maximum rate of ion transfer between the anode 114 and the cathode 112 from the reduced rate to the standard rate when the fault condition ends or is otherwise corrected. Accordingly, the anode 114 may act as a reversible fuse to prevent the electrochemical cell 110 from overheating. The fault condition may be corrected on its own, by an electrically coupled device or system, by an external device or system, by a user, etc. Correction of the fault condition may include, for example, the removal an electrical short, correction of programming errors, a change of parameter settings, etc.

Figure 3:
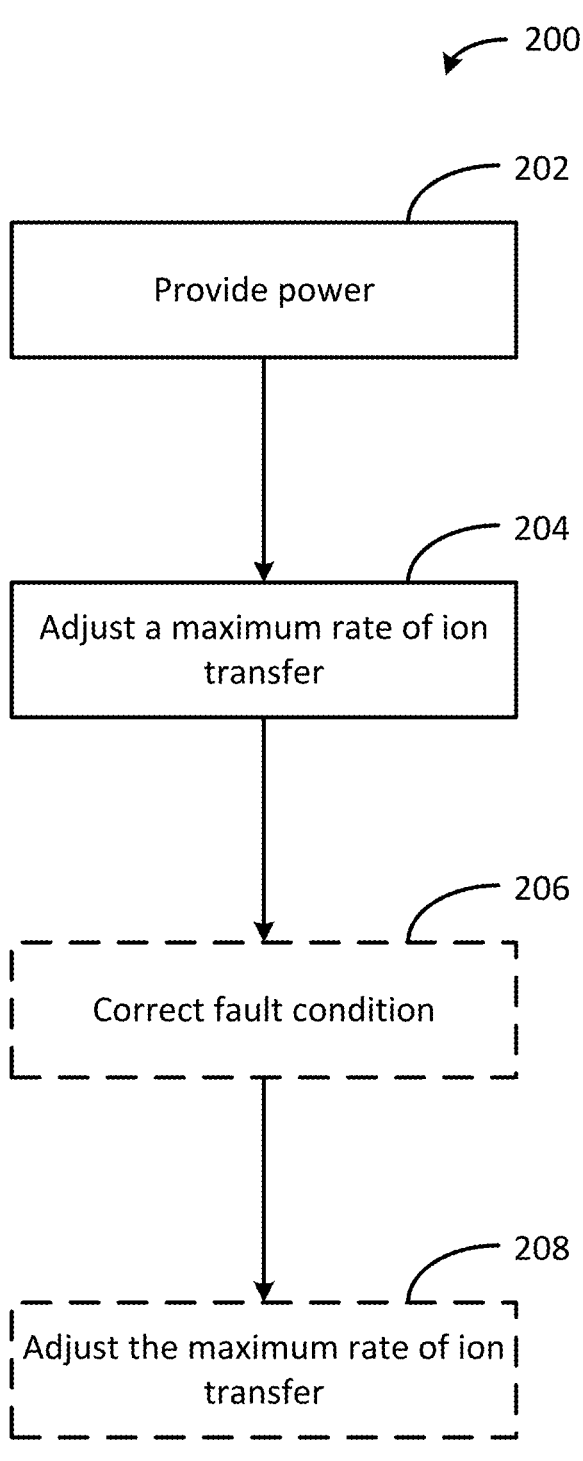
FIG. 3 is flow diagram of an embodiment of a method or process for preventing overheating of an electrochemical cell.

A method or process 200 for preventing overheating of an electrochemical cell (e.g., electrochemical cells 110 of FIGS. 1 and 2) is depicted in FIG. 3. The method 200 may include providing power using the electrochemical cell 202. The electrical power may be provided to electrical components of a device or system (e.g., device 100 of FIG. 1).

The method 200 may include adjusting, using an anode of the electrochemical cell, a maximum rate of ion transfer between a cathode and an anode of the electrochemical cell from a standard rate to a reduced rate in response to an occurrence of a fault condition 204. The anode may be used to adjust or reduce the maximum rate of ion transfer between the cathode and the anode by reducing the availability of lithium at surfaces of the anode for ion transport. For example, if power supplied by or drawn from the electrochemical cell is higher than a threshold amount and/or sustained for longer than a threshold period of time, the anode may take on the characteristics of an anode formed of a lithium alloy that contains less weight percent of lithium (e.g., 50 weight percent of lithium or less). With a reduction in the availability of lithium at surfaces of the anode, the maximum rate of ion transfer and the corresponding maximum power output of the electrochemical cell may be reduced.

The reduced rate may be rate of ion transfer that limits power output of the electrochemical cell to an amount that will prevent overheating of the electrochemical cell even if such power output is maintained for extended periods of time. In other words, a maximum power output of the electrochemical cell may be limited by the reduced rate of ion transfer such that maximum power output does not heat the electrochemical cell faster than such heat can be dissipated from the electrochemical cell.

The fault condition may include any condition that causes the electrochemical cell to provide power in excess of what is expected under typical device or system operation. The fault condition may include an electrical short in the electrochemical cell or electronic components or devices to which electrochemical cell provides power. The fault condition may also include any condition that causes the electrochemical cell to provide power above a threshold amount for a predetermined period of time. Such conditions may include programming errors in an electrically coupled device or system (e.g., device 100 of FIG. 1), mechanical failures of the electrically coupled device or system, unexpected parameter settings of the electrically coupled device or system, mechanical failures of the electrochemical cell, etc. The threshold amount may be an amount of power that is capable of heating the electrochemical cell faster than heat can dissipate from the electrochemical cell.

The method 200 may optionally include correcting the fault condition 206. The fault condition may be corrected on its own, by an electrically coupled device or system, by an external device or system, by a user, etc. Correcting the fault condition may include, for example, removing an electrical short, correction of programming errors, changing parameter settings, etc.

The method 200 may also optionally include adjusting, using the anode, the maximum rate of ion transfer from the reduced rate to the standard rate in response to the fault condition being corrected the 208. In other words, if the fault condition is corrected, the reduction in the maximum rate of ion transfer may be reversed.

It has been found that the use of some lithium alloys in anodes of electrochemical cells has the surprising effect of reducing the current that can be provided and heat generated by the electrochemical cells when power above a threshold amount is provided for extended periods of time. The results of experimentally pulsing electrochemical cells that include 10 weight percent magnesium in the anode of such cells is depicted in a graph 300 of FIG. 4. Voltage measurements over time of electrochemical cells having anodes that include 10 weight percent of magnesium are shown in graph 300. Data points represented by a dot correspond to current pulses at 2.5 milliamps per centimeter squared ($mA/cm^2$) and data points represented by a diamond correspond to current pulses at 0.5 milliamps per centimeter squared ($mA/cm^2$). As shown, the electrochemical cells underwent a sudden polarization resistance as indicated by the spikes in voltage after about 1.5 hours of pulsing at a failure condition current of 2.5 milliamps per centimeter squared. However, pulsing at a typical operating range current of 0.5 $mA/cm^2$, the electrochemical cells operated for 10 hours without a spike in voltage. Accordingly, the results indicate that there was no spike in resistance at currents within a typical operating range for the electrochemical cells.

The experimental results depicted in graph 300 were unexpected. However, it was realized that such results indicated that anodes that include a lithium alloy may allow electrochemical cells (e.g., electrochemical cell 110 of FIG. 2) to be designed for high power applications while providing overheat protection in the event a fault condition occurs. Additionally, the built-in overheat protection may allow for electrochemical cell designs that have greater anode and cathode surface areas relative to electrochemical cell designs of the same volume and form factor that limit anode and cathode surface areas as a form of overheat protection.

Figure 4:
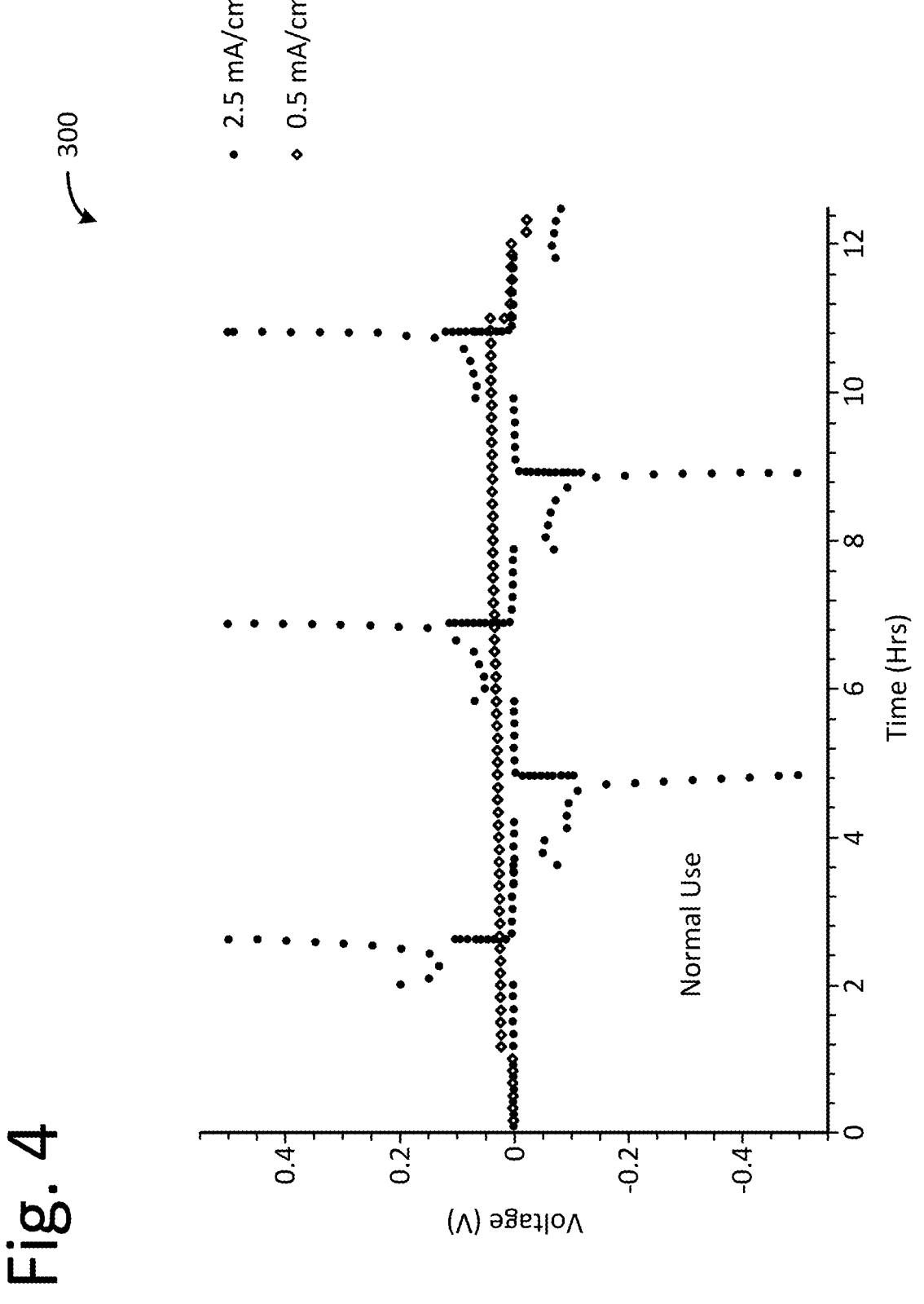
FIG. 4 is a graph depicting measured voltages over time of an electrochemical cell according to embodiments described herein.

Additional experimentation confirmed the results and inferences derived from the experimental results of FIG. 4. Two 2032 size coin cells were built, one with a traditional substantially pure lithium anode and one with an anode consisting of a lithium alloy with 90 weight percent lithium and 10 weight percent magnesium in the form of a 0.004-inch-thick foil. Both cells were identical in all other respects. The cathodes of each cell were a hybrid mixture of carbon monofluoride and silver vanadium oxide having a stoichiometric ratio of 2:1. The electrolyte of each cell was 1 molar $LiAsF_6$ in a 50/50 mixture of propylene carbonate/dimethyl carbonate. The separator of each cell was a 25-micrometer thick monolayer microporous membrane. The cathode and anode of each cell each had a surface area of 2 square centimeters. Both cells were burned in by discharging at 1 milliamp for a 3-hour period prior to pulse testing.

Pulse testing was carried on an Arbin BT2000 battery cycler in a controlled resistance mode. Both cells were subject to three different series of discharge pulses. One series of discharge pulses had an applied load of 100 ohms, a second series had an applied load of 50 Ohms, and a third series of discharge pulses had an applied load of 25 Ohms, with at least one day allowed for recovery in between each series. Pulse power was computed by multiplying the load voltage by delivered current and cumulative pulse energy at 30 seconds was computed by integrating the power over time.

As shown in the summary of results in Table 1 below, both cells delivered comparable energy under 100 Ohm loads.

TABLE 1

| External Load | Li-Mg Alloy | Li | Ratio (Alloy versus Li) |
|---|---|---|---|
| 100 Ohm | 1.87 Joules | 1.98 Joules | 95% |
| 50 Ohm | 2.54 Joules | 3.37 Joules | 75% |
| 25 Ohm | 2.27 Joules | 4.48 Joules | 51% |

However, as the pulse current increased due to the reduction in the load to 50 Ohms and 25 Ohms, respectively, cell behavior of the two cells differs. Whereas the lithium anode delivers more and more energy and, therefore, heat as the applied resistance is decreased, the lithium alloy anode goes through a local maximum at 50 Ohm and delivers substantially less energy than the lithium anode at 25 Ohm. The lithium alloy cell had nearly equivalent performance at 100 Ohms, delivering 95 percent of the energy that the lithium cell did under the same conditions. However, the ratio of energy delivered for the lithium alloy cell compared to the pure lithium cell, decreases to 75 percent and 51 percent as the load decreases to 50 Ohms and 25 Ohms, respectively.

Figure 5:
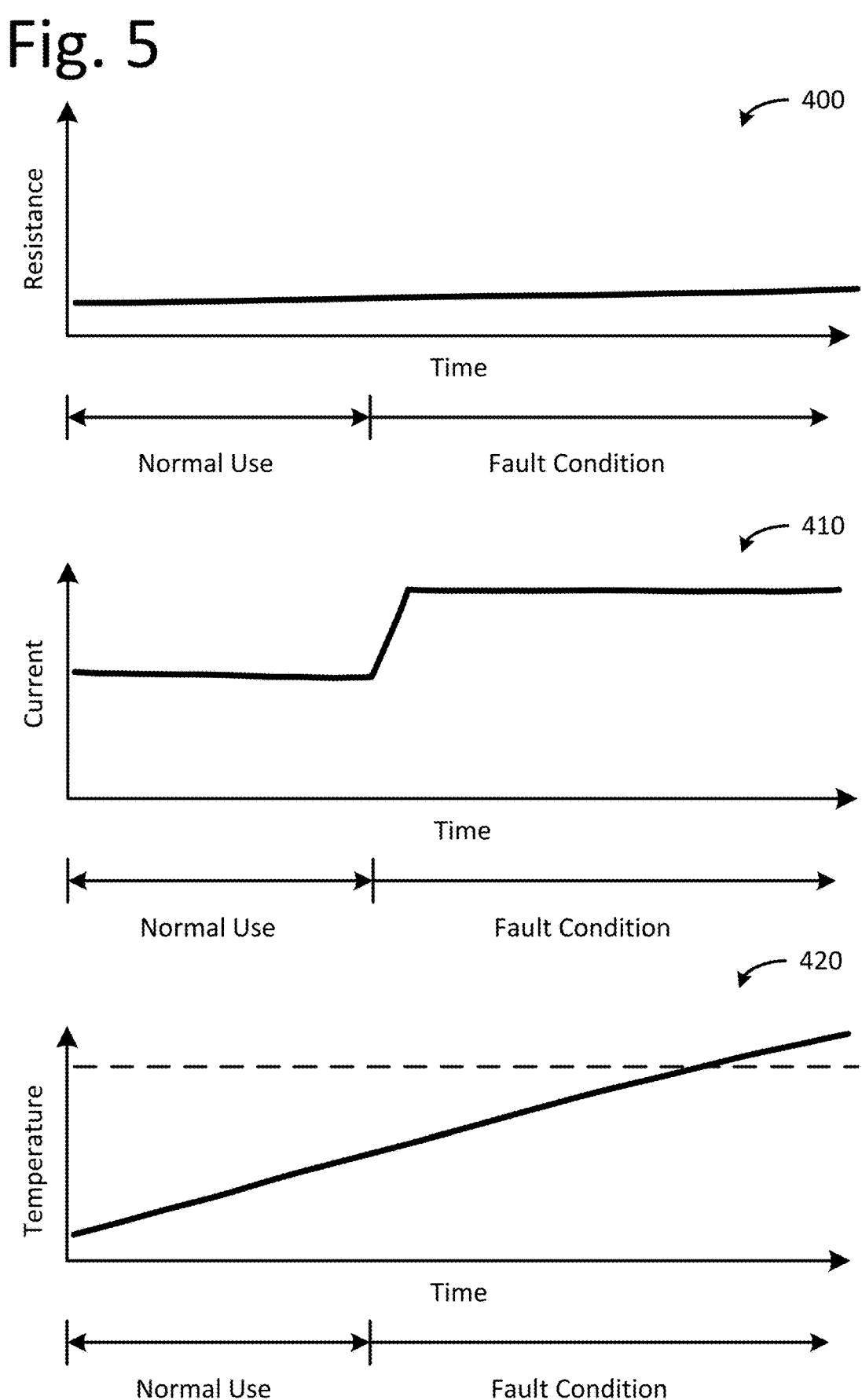
FIG. 5 is a set of graphs depicting measurements of a typical electrochemical cell during normal operating conditions and during a fault condition.
Figure 6:
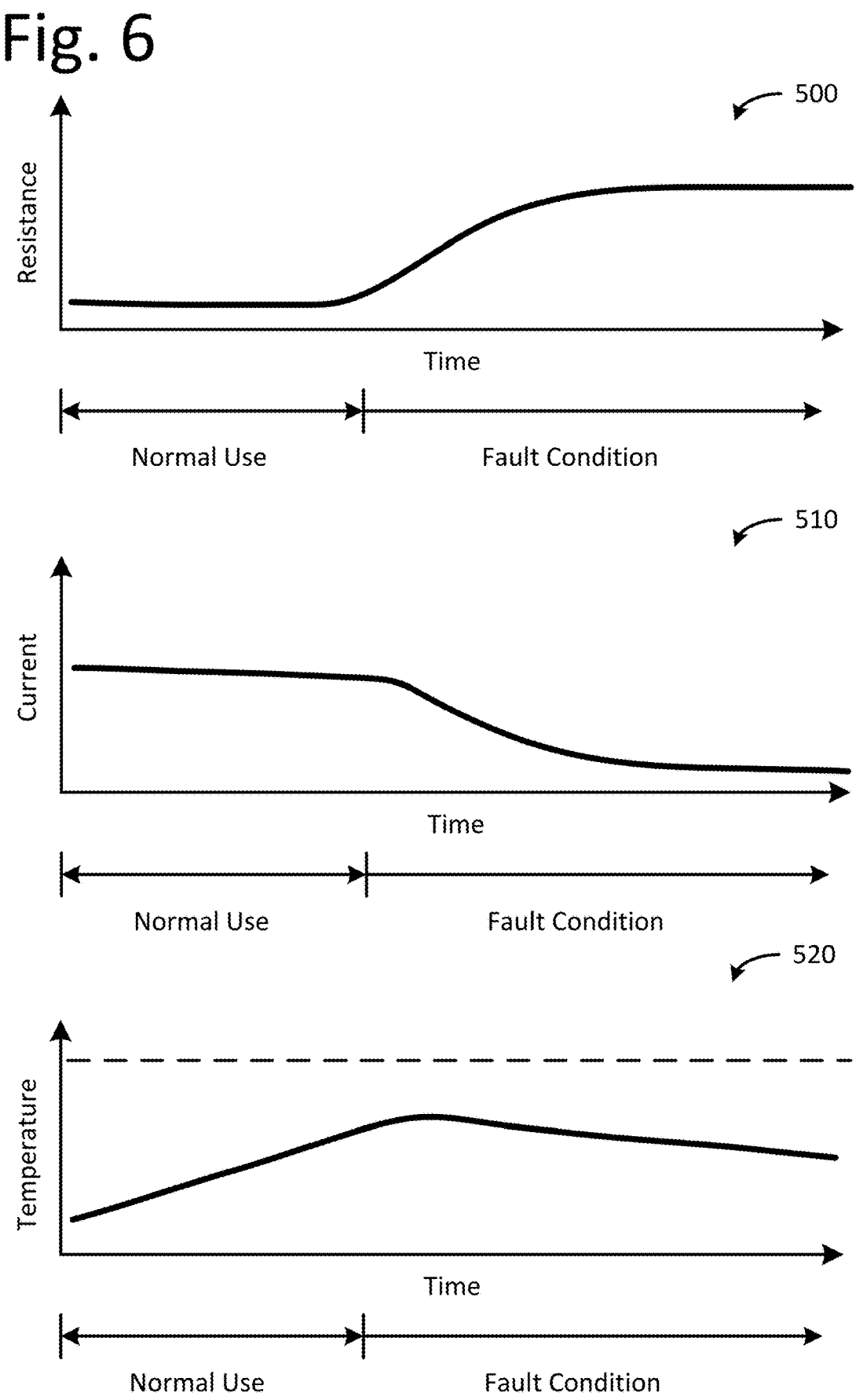
FIG. 6 is a set of graphs depicting measurements of an electrochemical cell with a lithium alloy anode during normal operating conditions and during a fault condition.

Additional details are depicted in the graphs of FIGS. 5 and 6. FIG. 5 shows a set of graphs 400, 410, 420 that each depict measurements of the pure lithium cell during normal operating conditions and during a fault condition. Graph 400 plots resistance over time, graph 410 plots current over time, and graph 420 plots temperature over time. FIG. 6 shows a set of graphs 500, 510, 520 that each depict measurements of the lithium alloy cell during normal operating conditions and during a fault condition. Graph 500 plots resistance over time, graph 510 plots current over time, and graph 520 plots temperature over time. In graphs 420, 520, the dashed line represents a temperature safety limit.

As shown in graphs 400, the resistance of the pure lithium cell remains constant in response to the occurrence of a fault condition. However, as shown in graph 410, the current increases sharply in response to the occurrence of the fault condition before leveling off at a maximum possible current of the pure lithium cell. Accordingly, as shown in graph 420, the temperature of the pure lithium cell continues to increase and exceeds the temperature safety limit. In contrast, as shown in graphs 500, 510, the resistance or the lithium alloy cell increases and a corresponding drop in current in observed. Accordingly, as shown in graph 520, the temperature increase levels off and begins to decrease during the fault condition and the temperature of the lithium alloy cell remains below the temperature safety limit.

These results indicate that the lithium alloy cell will perform comparably to a pure lithium cell under normal or typical operating conditions, yet deliver a twofold reduction in energy and, therefore, power under a low resistance fault condition, leading to a commensurate reduction in heat generation. Thus, electrochemical cells having anodes with lithium alloys as described herein may have improved thermal safety without significantly compromising performance.

The invention is defined in the claims. However, below there is provided a non-exhaustive list of non-limiting examples. Any one or more of the features of these examples may be combined with any one or more features of another example, embodiment, or aspect described herein.

Example Ex1: An electrochemical cell comprising: a cathode; and an anode comprising a lithium alloy and configured to reduce a maximum rate of ion transfer between the anode and the cathode from a standard rate to a reduced rate in response to an occurrence of a fault condition, the lithium alloy comprising at least 70 weight percent lithium to 99 weight percent lithium.

Example Ex2: The electrochemical cell as in example Ex1, wherein the lithium alloy comprises 1 weight percent to 30 weight percent of magnesium.

Example Ex3: The electrochemical cell as in example Ex1, wherein the lithium alloy comprises 5 weight percent to 15 weight percent of magnesium.

Example Ex4: The electrochemical cell as in example Ex1, wherein the lithium alloy is a binary alloy.

Example Ex5: The electrochemical cell as in example Ex1, wherein the lithium alloy consists essentially of lithium and magnesium.

Example Ex6: The electrochemical cell as in example Ex1, wherein the lithium alloy consists of lithium and magnesium.

Example Ex7: The electrochemical cell as in example Ex1, wherein the lithium alloy comprises one or more of magnesium, silver, zinc, aluminum, tin, and silicon.

Example Ex8: The electrochemical cell as in example Ex1, wherein the lithium alloy consists essentially of lithium and one or more of magnesium, silver, zinc, aluminum, tin, and silicon.

Example Ex9: The electrochemical cell as in example Ex1, wherein the lithium alloy consists of lithium and one or more of magnesium, silver, zinc, aluminum, tin, and silicon.

Example Ex10: The electrochemical cell as in example Ex1, wherein the fault condition comprises electrical power provided by the electrochemical cell exceeding a threshold level for a predetermined period of time.

Example Ex11: The electrochemical cell as in example Ex1, wherein the fault condition comprises an electrical short.

Example Ex12: The electrochemical cell as in example Ex1, wherein the anode is further configured to reverse the reduction of the maximum rate of ion transfer in response to a correction of the fault condition.

Example Ex13: The electrochemical cell as in example Ex1, further comprising: a separator arranged between the anode and the cathode to prevent direct contact between the anode and the cathode; and an electrolyte to facilitate transport of charged ions between the anode and the cathode.

Example Ex14: The electrochemical cell as in example Ex1, wherein the anode further comprises an anode core and the lithium alloy defines an outer surface layer of the anode.

Example Ex15: The electrochemical cell as in example Ex1, wherein the anode further comprises an anode core and the lithium alloy completely surrounds the anode core.

Example Ex16: The electrochemical cell as in example Ex1, wherein the anode further comprises an anode core and the anode comprises at least 70 weight percent lithium and no greater than 99 weight percent lithium.

Example Ex17: An implantable medical device comprising: a housing; one or more electrical components disposed in the housing; and one or more electrochemical cells electrically coupled to at least one electrical component of the one or more electrical components, each of the one or more electrochemical cells comprising: a cathode; an anode comprising a lithium alloy and configured to reduce a maximum rate of ion transfer between the anode and the cathode from a standard rate to a reduced rate in response to an occurrence of a fault condition, the lithium alloy comprising at least 70 weight percent lithium to 99 weight percent lithium; a separator arranged between the anode and the cathode to prevent direct contact between the anode and the cathode; and an electrolyte to facilitate transport of ions between the anode and the cathode.

Example Ex18: The implantable medical device as in example Ex17, wherein the implantable medical device comprises an implantable cardioverter defibrillator.

Example Ex19: The implantable medical device as in example Ex17, wherein the fault condition comprises providing a current, using the electrochemical cell, equal to or greater than a threshold current for a threshold period of time.

Example Ex20: The implantable medical device as in example Ex19, wherein the implantable medical device is configured to deliver therapeutic electrical pulses, wherein the at least one electrical component is configured to draw energy from each of the one or more electrochemical cells at a pulse current level for a predetermined time period, and wherein the threshold current is less than or equal to the pulse current and the threshold period of time is greater than the predetermined time period.

Example Ex21: The implantable medical device as in example Ex17, wherein the anode comprises 5 weight percent to 15 weight percent of magnesium.

Example Ex22: The implantable medical device as in example Ex17, wherein the lithium alloy comprises 0.1 weight percent to 30 weight percent of magnesium.

Example Ex23: The implantable medical device as in example Ex17, wherein the lithium alloy comprises 5 weight percent to 15 weight percent of magnesium.

Example Ex24: The implantable medical device as in example Ex17, wherein the lithium alloy is a binary alloy.

Example Ex25: The implantable medical device as in example Ex17, wherein the lithium alloy consists essentially of lithium and magnesium.

Example Ex26: The implantable medical device as in example Ex17, wherein the lithium alloy consists of lithium and magnesium.

Example Ex27: The implantable medical device as in example Ex17, wherein the lithium alloy comprises one or more of magnesium, silver, zinc, aluminum, tin, and silicon.

Example Ex28: The implantable medical device as in example Ex17, wherein the lithium alloy consists essentially of lithium and one or more of magnesium, silver, zinc, aluminum, tin, and silicon.

Example Ex29: The implantable medical device as in example Ex17, wherein the lithium alloy consists of lithium and one or more of magnesium, silver, zinc, aluminum, tin, and silicon.

Example Ex30: The implantable medical device as in example Ex17, wherein the fault condition comprises electrical power provided by the electrochemical cell exceeding a threshold level for a predetermined period of time.

Example Ex31: The implantable medical device as in example Ex17, wherein the fault condition comprises an electrical short.

Example Ex32: The implantable medical device as in example Ex17, wherein the anode is further configured to reverse the reduction of the maximum rate of ion transfer in response to correction of the fault condition.

Example Ex33: The implantable medical device as in example Ex17, wherein the anode further comprises an anode core and the lithium alloy defines an outer surface layer of the anode.

Example Ex34: The implantable medical device as in example Ex17, wherein the anode further comprises an anode core and the lithium alloy completely surrounds the anode core.

Example Ex35: The implantable medical device as in example Ex17, wherein the anode further comprises an anode core and the anode comprises at least 70 weight percent lithium and no greater than 99 weight percent lithium.

Example Ex36: A method for preventing overheating of an electrochemical cell, the electrochemical cell comprising: a cathode; an anode comprising a lithium alloy, the lithium alloy comprising at least 70 weight percent lithium to 99 weight percent lithium; a separator arranged between the cathode and the anode to prevent direct contact between the anode and the cathode; and an electrolyte to facilitate transport of ions between the cathode and the anode; and the method comprising: providing power using the electrochemical cell; and adjusting, using the anode, a maximum rate of ion transfer between the cathode and the anode from a standard rate to a reduced rate response to an occurrence of a fault condition.

Example Ex37: The method as in example Ex36, further comprising: correcting the fault condition; and adjusting, using the anode, the maximum rate of ion transfer from the reduced rate to the standard rate in response to the fault condition being corrected.

Example Ex38: The method as in example Ex37, wherein the lithium alloy comprises 0.1 weight percent to 30 weight percent of magnesium.

Example Ex39: The method as in example Ex37, wherein the lithium alloy comprises 5 weight percent to 15 weight percent of magnesium.

Example Ex40: The method as in example Ex37, wherein the lithium alloy is a binary alloy.

Example Ex41: The method as in example Ex37, wherein the lithium alloy consists essentially of lithium and magnesium.

Example Ex42: The method as in example Ex37, wherein the lithium alloy consists of lithium and magnesium.

Example Ex43: The method as in example Ex37, wherein the lithium alloy comprises one or more of magnesium, silver, zinc, aluminum, tin, and silicon.

Example Ex44: The method as in example Ex37, wherein the lithium alloy consists essentially of lithium and one or more of magnesium, silver, zinc, aluminum, tin, and silicon.

Example Ex45: The method as in example Ex37, wherein the lithium alloy consists of lithium and one or more of magnesium, silver, zinc, aluminum, tin, and silicon.

Example Ex46: The method as in example Ex37, wherein the fault condition comprises electrical power provided by the electrochemical cell exceeding a threshold amount for a predetermined period of time.

Example Ex47: The method as in example Ex37, wherein the anode further comprises an anode core and the lithium alloy defines an outer surface layer of the anode.

Example Ex48: The method as in example Ex37, wherein the anode further comprises an anode core and the lithium alloy completely surrounds the anode core.

Example Ex49: The method as in example Ex37, wherein the anode further comprises an anode core and the anode comprises at least 70 weight percent lithium and no greater than 99 weight percent lithium.

All scientific and technical terms used herein have meanings commonly used in the art unless otherwise specified. The definitions provided herein are to facilitate understanding of certain terms used frequently herein and are not meant to limit the scope of the present disclosure.

As used herein, singular forms "a," "an" and "the" include plural referents unless the context clearly dictates otherwise. As used in this specification and the appended claims, the term "or" is generally employed in its sense including "and/or" unless the content clearly dictates otherwise. The term "and/or" means one or all of the listed elements or a combination of any two or more of the listed elements.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the inventive technology.

As used herein, "have", "having", "include", "including", "comprise", "comprising" or the like are used in their open ended sense, and generally mean "including, but not limited to." It will be understood that the terms "consisting of" and "consisting essentially of" are subsumed in the term "comprising." For example, a microfluidic device comprising a sheet having an interconnected microporous structure, a double-sided adhesive layer, and a film may consist of, or consist essentially of, the sheet, the adhesive layer and the film.

As used herein, "consisting essentially of", as it relates to a compositions, articles, systems, apparatuses or methods, means that the compositions, articles, systems, apparatuses or methods include only the recited components or steps of the compositions, articles, systems, apparatuses or methods and, optionally, other components or steps that do not materially affect the basic and novel properties of the compositions, articles, systems, apparatuses or methods.

The term "substantially" as used here has the same meaning as "significantly," and can be understood to modify the term that follows by at least about 90 percent, at least about 95 percent, or at least about 98 percent. The term "substantially free" of a particular compound means that the compositions of the present invention contain less than 1,000 parts per million (ppm) of the recited compound. The term "essentially free" of a particular compound means that the compositions of the present invention contain less than 100 parts per million (ppm) of the recited compound. The term "completely free" of a particular compound means that the compositions of the present invention contain less than 20 parts per billion (ppb) of the recited compound. In the context of the aforementioned phrases, the compositions of the present invention contain less than the aforementioned amount of the compound whether the compound itself is present in unreacted form or has been reacted with one or more other materials.

As used herein, the term "not substantially" has the same meaning as "not significantly," and can be understood to have the inverse meaning of "substantially," i.e., modifying the term that follows by not more than 25 percent, not more than 10 percent, not more than 5 percent, or not more than 2 percent.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred. Any recited single or multiple feature or aspect in any one claim can be combined or permuted with any other recited feature or aspect in any other claim or claims.

It will be apparent to those skilled in the art that various modifications and variations can be made to the present inventive technology without departing from the spirit and scope of the disclosure. Since modifications, combinations, sub-combinations and variations of the disclosed embodiments incorporating the spirit and substance of the inventive technology may occur to persons skilled in the art, the inventive technology should be construed to include everything within the scope of the appended claims and their equivalents.

What is claimed is:

1. An electrochemical cell for an implantable medical device, the electrochemical cell comprising:
   a cathode; and
   an anode comprising a lithium alloy and configured to reduce a maximum rate of ion transfer between the anode and the cathode from a standard rate to a reduced rate in response to an occurrence of a fault condition, the lithium alloy comprising at least 70 weight percent lithium to 99 weight percent lithium, the fault condition comprising providing a current, using the electrochemical cell, equal to or greater than a threshold current for a threshold period of time, wherein the implantable medical device is configured to deliver electrical pulses and to draw energy from the electrochemical cell at a pulse current level for a predetermined time period, wherein the threshold current is less than or equal to the pulse current and the threshold period of time is greater than the predetermined time period.

2. The electrochemical cell as in claim 1, wherein the lithium alloy comprises 1 weight percent to 30 weight percent of magnesium.

3. The electrochemical cell as in claim 1, wherein the lithium alloy comprises 5 weight percent to 15 weight percent of magnesium.

4. The electrochemical cell as in claim 1, wherein the lithium alloy consists essentially of lithium and magnesium.

5. The electrochemical cell as in claim 1, wherein the lithium alloy consists of lithium and magnesium.

6. The electrochemical cell as in claim 1, wherein the fault condition comprises electrical power provided by the electrochemical cell exceeding a threshold level for a predetermined period of time.

7. An implantable medical device comprising:

a housing;

one or more electrical components disposed in the housing; and one or more electrochemical cells electrically coupled to at least one electrical component of the one or more electrical components, each of the one or more electrochemical cells comprising:

a cathode;

an anode comprising a lithium alloy and configured to reduce a maximum rate of ion transfer between the anode and the cathode from a standard rate to a reduced rate in response to an occurrence of a fault condition, the lithium alloy comprising at least 70 weight percent lithium to 99 weight percent lithium, the fault condition comprising providing a current, using the electrochemical cell, equal to or greater than a threshold current for a threshold period of time;

a separator arranged between the anode and the cathode to prevent direct contact between the anode and the cathode; and an electrolyte to facilitate transport of ions between the anode and the cathode, wherein the implantable medical device is configured to deliver therapeutic electrical pulses, wherein the at least one electrical component is configured to draw energy from each of the one or more electrochemical cells at a pulse current level for a predetermined time period, and wherein the threshold current is less than or equal to the pulse current and the threshold period of time is greater than the predetermined time period.

8. The implantable medical device as in claim 7, wherein the implantable medical device comprises an implantable cardioverter defibrillator.

9. A method for preventing overheating of an electrochemical cell for an implantable medical device, the electrochemical cell comprising:

a cathode;

an anode comprising a lithium alloy, the lithium alloy comprising at least 70 weight percent lithium to 99 weight percent lithium;

a separator arranged between the cathode and the anode to prevent direct contact between the anode and the cathode; and an electrolyte to facilitate transport of ions between the cathode and the anode; and the method comprising:

providing power using the electrochemical cell; and adjusting, using the anode, a maximum rate of ion transfer between the cathode and the anode from a standard rate to a reduced rate response to an occurrence of a fault condition, the fault condition comprising providing a current, using the electrochemical cell, equal to or greater than a threshold current for a threshold period of time; and wherein the implantable medical device is configured to deliver electrical pulses to draw energy from the electrochemical cell at a pulse current level for a predetermined time period, wherein the threshold current is less than or equal to the pulse current and the threshold period of time is greater than the predetermined time period.

10. The method as in claim 9, further comprising:

correcting the fault condition; and adjusting, using the anode, the maximum rate of ion transfer from the reduced rate to the standard rate in response to the fault condition being corrected.

11. The method as in claim 10, wherein the lithium alloy comprises 0.1 weight percent to 30 weight percent of magnesium.

12. The method as in claim 10, wherein the lithium alloy comprises 5 weight percent to 15 weight percent of magnesium.

13. The method as in claim 10, wherein the lithium alloy is a binary alloy.

14. The method as in claim 10, wherein the lithium alloy consists essentially of lithium and magnesium.

15. The method as in claim 10, wherein the lithium alloy consists of lithium and magnesium.

16. The method as in claim 10, wherein the lithium alloy comprises one or more of magnesium, silver, zinc, aluminum, tin, and silicon.

17. The method as in claim 10, wherein the lithium alloy consists essentially of lithium and one or more of magnesium, silver, zinc, aluminum, tin, and silicon.

18. The method as in claim 10, wherein the fault condition comprises electrical power provided by the electrochemical cell exceeding a threshold amount for a predetermined period of time.

* * * * *